United States Patent [19]

Harrison et al.

[11] Patent Number: 4,717,569

[45] Date of Patent: Jan. 5, 1988

[54] UNIT DOSAGE FORM OF SPARINGLY SOLUBLE MEDICAMENTS

[75] Inventors: Paul J. Harrison; John R. Langridge; Christopher J. Potter, all of Alnwick, England

[73] Assignee: Sterling Drug Inc., New York, N.Y.

[21] Appl. No.: 738,104

[22] Filed: May 24, 1985

[30] Foreign Application Priority Data

Jun. 4, 1984 [GB] United Kingdom ............... 8414221

[51] Int. Cl.$^4$ ................. A61K 9/14; A61K 31/57; A61K 31/565
[52] U.S. Cl. ................................ 424/494; 424/497; 514/172; 514/176
[58] Field of Search ............... 514/179, 180, 172, 176; 424/494, 497

[56] References Cited

U.S. PATENT DOCUMENTS

| | | | |
|---|---|---|---|
| 3,328,256 | 6/1967 | Gaunt | 514/179 |
| 4,361,546 | 11/1982 | Stricker et al. | 424/19 |
| 4,367,217 | 1/1983 | Gruber et al. | 424/19 |
| 4,389,393 | 6/1983 | Schor et al. | 514/180 |
| 4,415,547 | 11/1983 | Yu et al. | 424/19 |
| 4,438,091 | 3/1984 | Gruber et al. | 424/19 |

FOREIGN PATENT DOCUMENTS

| | | |
|---|---|---|
| 61217 | 9/1982 | European Pat. Off. . |
| 2458112 | 2/1976 | Fed. Rep. of Germany . |
| 742007 | 12/1955 | United Kingdom . |
| 765086 | 1/1957 | United Kingdom . |
| 785262 | 10/1957 | United Kingdom . |
| 844772 | 8/1960 | United Kingdom . |
| 1326995 | 8/1973 | United Kingdom . |
| 1469133 | 3/1977 | United Kingdom . |
| 1561301 | 2/1980 | United Kingdom . |
| 2105724 | 3/1983 | United Kingdom ............... 514/179 |

OTHER PUBLICATIONS

Chem. Abst. 103:128939(a) (1985)–Urtti et al.
Lachman et al., The Theory and Practice of Industrial Pharmacy, 2nd ed., pp. 456–459.

*Primary Examiner*—Douglas W. Robinson
*Attorney, Agent, or Firm*—William G. Webb; Paul E. DuPont

[57] ABSTRACT

Pharmaceutical compositions of a polycyclic medicament having very low solubility in water and aqueous media comprise a plurality of beads, each bead comprising particles of finely divided medicament, which may have a particulate core or filler, bound together by a water soluble binder.

7 Claims, 2 Drawing Figures

UNIT DOSAGE FORM OF SPARINGLY SOLUBLE MEDICAMENTS

BACKGROUND OF THE INVENTION

This invention relates to pharmaceutical compositions of polycyclic medicaments which have a solubility in water and aqueous media of less than 1 part by weight of the medicament in from 5,000 to greater than 10,000 parts by weight of the medium at ambient temperatures.

INFORMATION DISCLOSURE STATEMENT

The low solubility of a number of medicaments having a polycyclic structure in aqueous media is a source of inconvenience and raises the overall cost of a course of treatment with any one of these drugs. Typical of these medicaments are synthetic steroidal agents, such as 17α-pregna-2,4-diene-20-yno[2,3-d]isoxazol-17-ol which is known to be highly insoluble in water and which is usually given to patients in the form of a dry powder in a capsule. This material, which inhibits the synthesis or release of pituitary gonadotrophins without exhibiting oestrogenic or progestational activity in patients, has been administered in doses of 200 to 800 mg. per day. The medicament has been synthesised from ethisterone, supplies of which have been limited. It is therefore desirable that the medicament should be given to patients in a form in which it is most efficiently utilised by the body. Similar problems arise in the case of a number of other steroidal medicaments, and there is thus a great need for dosage forms of such water insoluble medicaments that will ensure production of rapid and high plasma concentrations of the medicaments.

The prior art, however, provides little guidance to overcoming the problem.

Thus U.S. Pat. No. 4,361,546 discloses sustained release compositions containing a disintegrating core which comprises a medicament in a water soluble form with a water soluble coating and a plurality of non-disintegrating cores comprising the medicament in water soluble form with a coating consisting of a water insoluble film former and a water soluble polymer.

U.S. Pat. No. 4,367,217 discloses a sustained release form of dipyridamole comprising spheroid particles of the same, or acid-addition salts thereof, and an acid or an acidic substance; and a coating surrounding the spheroids comprising an acid insoluble first lacquer, which is soluble in the intestinal juices, and a second lacquer which is insoluble in gastric and intestinal juices. The coated spheroid particles are then filled into gelatine capsules. Because of the acid nature of the medium within the sustained release form, the dipyridamole diffuses out of the insoluble coat in the relatively alkaline environment (pH 6.0-7.0) of the intestinal juices despite the fact that the dipyridamole is insoluble at such pH levels.

U.S. Pat. No. 4,415,547 discloses a sustained release preparation for release in the alimentary canal comprising nonpareils coated first with the drug agent, then with a water soluble drug binding substance, such as hydroxypropylmethylcellulose, and then with a second water soluble film former, for example hydroxypropylmethylcellulose. The resulting pellets are then mixed with a diluent and a binder, such as ethyl cellulose, and pressed into tablets.

U.S. Pat. No. 4,438,091 discloses generally the same approach as that described in U.S. Pat. No. 4,367,217 discussed above but adapted to the sustained release of bromhexine. That is, spheroid particles of an acid-addition salt of bromhexine are coated with a first lacquer, which is insoluble in gastric juices and soluble in intestinal juices, and a second lacquer, which is insoluble in gastric and intestinal juices, to produce a diffusion membrane. The coated spheroids are then packed into gelatine capsules or pressed into tablets. The lacquered membrane does not break down in the digestive tract but only allows diffusion of the drug therethrough.

SUMMARY OF THE INVENTION

It is an object of this invention to provide a formulation of insoluble medicaments in which the relative bioavailability of the medicaments, especially steroidal medicaments, is substantially enhanced.

The invention provides a pharmaceutical composition for oral administration of a polycyclic medicament having a solubility in water and aqueous media at ambient temperatures of less than 1 part of the medicament in from 5,000 to greater than 10,000 parts by weight of the medium which comprises a plurality of beads, each bead comprising particles of finely divided solid medicament bound together by a binder soluble in water and aqueous media at all pH values normally found in the gastrointestinal tract, and preferably a pharmacologically acceptable wetting agent, said plurality of beads together constituting a unit dose. In a preferred embodiment, the unit dosage form is enclosed in a gastric juice-soluble material, such as gelatin.

DETAILED DESCRIPTION INCLUSIVE OF THE PREFERRED EMBODIMENTS

Figure 1:
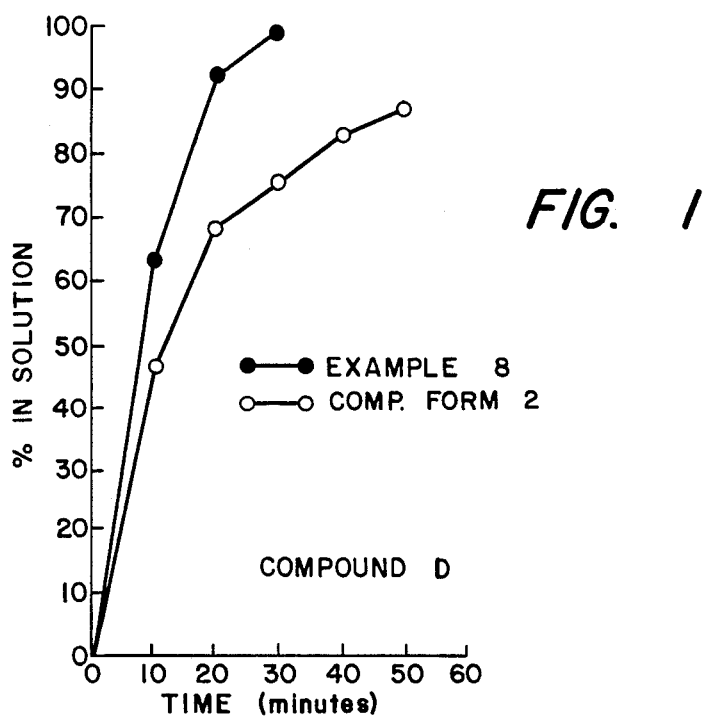

Thus in accordance with the present invention, each of the plurality of beads may comprise a core consisting of one or more nonpareils each of which has adherent thereto, by the action of a binder, a coating of finely divided particles of said medicament.

In a preferred unit dosage form, a predetermined quantity of the thus prepared beads is then used to fill capsules after which the capsules are closed and are then ready for administration.

A number of steroidal compounds having the indicated low solubility in water have the general formula I:

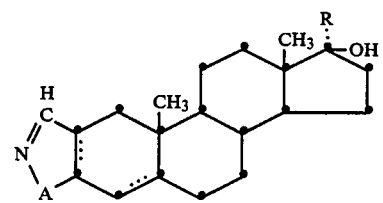

in which R is a lower-alkyl, lower-alkenyl or lower-alkynyl group having from 1 to 4 carbon atoms, A is an oxygen atom or a group of the formula —N—B where B is a hydrogen atom, a para-fluorophenyl group or a double bond. The production of such compounds is described in British Patent Specifications Nos. 905,844; 911,814 and 1,184,400. These compounds are steroidal isoxazoles and pyrazoles.

A second group of steroidal compounds having the indicated low solubility in water have the general formula II:

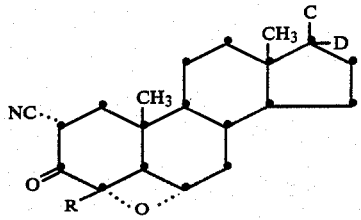

in which R is hydrogen or methyl, C is hydrogen or hydroxyl and D is hydrogen or a lower-alkyl, lower-alkenyl or lower alkynyl group having from 1 to 4 carbon atoms. The production of such compounds is described in British Patent Specifications Nos. 1,123,730 and 2,010,278A. These compounds are steroidal carbonitriles.

Typical examples of compounds having the above general formulae are 17α-pregna-2,4-diene-20-yno[2,3-d]isoxazol-17-ol (identified hereinafter as Compound A), 17β-hydroxy-17α-methylandrostano[3,2-c]pyrazole (identified hereinafter as Compound B), 17β-hydroxy-17α-ethynyl-4-androsteno[3,2-c]-2′-(para-fluoro-phenyl)pyrazole (identified hereinafter as Compound C), all of formula I, and 4α,5α-epoxy-17β-hydroxy-4,17-dimethyl-3-oxoandrostane-2α-carbonitrile (identified hereinafter as Compound D) and 4α,5α-epoxy-17β-hydroxy-3-oxoandrostane-2α-carbonitrile (identified hereinafter as Compound E), both of formula II.

The binders used in preparing the beads essential to the practice of the invention are soluble in water and aqueous media at pH values normally found in the gastrointestinal tract. Suitable binders for this purpose include polymeric cellulose derivatives, such as hydroxypropylmethylcellulose. Other binders include the sugars derived from sugar syrups and the water-soluble polysaccharides. Non-cellulosic binders which may be used include polyvinylpyrrolidone and vinylpyrrolidone copolymers such as those with vinyl acetate.

In the present unit dosage form, it has been found useful to include a filler or core material. The core material, when used, may conveniently be an inorganic or organic nonpareil such as titania, talc, dibasic calcium phosphate, microcrystalline cellulose, lactose or a sugar/starch bead.

On account of the low solubility of the medicaments used in the formulations of this invention and the consequent difficulty in wetting the particles thereof, it is preferred in formulating the products to include a surface active agent. Examples of suitable surface active agents are sodium lauryl sulphate and polyoxyethylene ethers of mixed partial oleic esters of sorbitol anhydrides. Other pharmaceutically acceptable non-ionic and anionic surface active agents may also be used.

The core is coated with particles of the medicament in solid form, after grinding if necessary in order to obtain particles of sufficiently small size to be conveniently adhered to particles of core material. A convenient size is that which will pass a 25 US mesh but be retained on a 30 US mesh. To adhere the particles of medicament to the core material, a suspension in an aqueous solution of one or more of the binders is prepared. The aqueous solution used preferably contains a wetting agent to ensure that the particles are thoroughly wetted. The resulting suspension is then used to coat the nonpareils in a coating column or coating pan, and the coated particles are then dried using a current of warm air.

The beads are then weighed out in amounts constituting a single dose, and each dose is then introduced into a gelatine capsule and the capsule then closed. Each capsule contains a unit dose consisting of beads in which small particles of medicament adhere either to a core or to other particles of medicament. Adhesion of the particles is by means of the binder used and this may contain a small proportion of wetting agent.

The following examples illustrate the invention, all parts being by weight unless otherwise specified.

EXAMPLE 1

The following were weighed out:

| | |
|---|---|
| Compound A | 100 parts |
| Hydroxypropylmethyl cellulose (6 cps)* | 50 parts |
| Nonpareils (sugar/starch) | 250 parts |

Here and elsewhere in this specification, the viscosities reports were determined at 2% aqueous solutions at 20° C.

A solution of the hydroxypropylmethylcellulose in water was prepared, and Compound A was dispersed therein. The nonpareils were placed in a coating column, and the solution gradually added thereto whilst passing a current of warm air through the column. After adding all the solution, warm air was passed until the coated particles were dry. The coated particles were weighed out into portions of 400 mg, and each portion was fed into a No. 1 size capsule and capped.

EXAMPLE 2

The following were weighed out:

| | |
|---|---|
| Compound A | 100 parts |
| Hydroxypropylmethyl cellulose (6 cps) | 30 parts |
| Nonpareils (sugar/starch) | 100 parts |
| Sodium lauryl sulphate | 1 part |

A solution of hydroxypropylmethylcellulose and sodium lauryl sulphate in water was prepared, and Compound A was dispersed therein. The nonpareils were placed in a coating column, and the solution was gradually added thereto whilst passing a current of warm air through the column. When all the solution had been introduced, warm air was passed until the coated particles were dry. The dried coated particles were weighed out into portions each weighing 231 mg, and each portion fed into a No. 2 size capsule and capped.

EXAMPLES 3–5

In a similar fashion, nonpareil beads (25/30 mesh) coated with Compound A were prepared from ingredients as follows and fed into gelatine capsules of the sizes indicated. All amounts are in milligrams per dose.

| Ingredient | Ex. 3 | Ex. 4 | Ex. 5 |
|---|---|---|---|
| Compound A | 100.0 | 100.0 | 100.0 |
| Hydroxypropylmethyl-cellulose (6 cps) | 20.0 | 20.0 | 20.0 |
| Sodium lauryl sulfate | 1.0 | 1.0 | 1.0 |
| Polyvinyl-pyrrolidone | 0.4 | 0.4 | 0.4 |
| Nonpareils | 278.6 | 238.6 | 178.6 |
| Total | 400.0 | 360.0 | 300.00 |

-continued

| Ingredient | Ex. 3 | Ex. 4 | Ex. 5 |
| --- | --- | --- | --- |
| Capsule Size | 1 | 1 | 1 |

EXAMPLES 6-9

In a similar fashion, nonpareil beads (25/30 mesh) coated with Compounds B, C, D or E, within the ambit of the invention, were prepared from ingredients as follows and fed into capsules of the sizes indicated. All amounts are in milligrams per dose.

| Ingredient | Ex. 6 | Ex. 7 | Ex. 8 | Ex. 9 |
| --- | --- | --- | --- | --- |
| Compound B | 5.0 | — | — | — |
| Compound C | — | 100.0 | — | — |
| Compound D | — | — | 100.0 | — |
| Compound E | — | — | — | 120.0 |
| Hydroxypropylmethyl cellulose (6 cps) | 2.0 | 30.0 | 30.0 | 49.0 |
| Sodium lauryl sulfate | 0.05 | 1.0 | 1.0 | 1.0 |
| Nonpareils | 143.0 | 229.0 | 229.0 | 150.0 |
| Total | 150.05 | 360.0 | 360.0 | 320.0 |
| Capsule size | 3 | 1 | 1 | 1 |

COMPARATIVE FORMULATION

A Comparative Formulation containing Compound A as the active ingredient, and comprising a conventional capsule formulation with starch, lactose, talc and magnesium stearate (Comparative Formulation 1) was formulated as follows and fed into gelatine capsules using conventional capsule procedures. All weights are in milligrams per dose.

| Ingredient | Comparative Formulation 1 |
| --- | --- |
| Compound A | 100.0 |
| Starch BP | 62.0 |
| Lactose BP | 62.0 |
| Talc BP | 5.0 |
| Magnesium stearate BP | 1.0 |
| Total | 230.0 |

| Ingredient | Comparative Formulation 1 |
| --- | --- |
| Capsule size | 3 |

A comparative bioavailability study of Comparative Formulation 1 and the formulation of Example 1 above was carried out in eight male volunteers, ages 22-42, in a randomized cross-over study, the formulations being designated as follows:

| Formulation | Corresponds to |
| --- | --- |
| A | 1 capsule of Comparative Formulation 1 |
| B | 1 capsule of formulation of Example 1 |

Each formulation thus contained 100 mg. of the active medicament of Compound A and was administered with 100 ml. of tap water following an overnight fast. Blood samples were taken pre-medication and at 0.25, 0.5, 1.0, 1.5, 2.0, 3.0, 4.0, 6.0, 8.0 and 10.0 hours post-medication. The samples were centrifuged, and plasma was separated and stored between $-15°$ C. and $-20°$ C. pending assay for Compound A by a validated HPLC procedure.

Regression analysis of peak area ratios (active ingredient/internal standard) with respect to concentration was performed for known calibration standards made up in control plasma. The resulting linear regression was used to determine the plasma concentrations of the active ingredient from the volunteer samples. The data so-obtained with Comparative Formulation 1 and the formulation of Example 1 are given in Tables 1 and 2.

Differences in plasma concentrations were apparent at all times from 0.75 to 6.0 hours. In the tables which follow, S.D. represents Standard Deviation, and C of V represents Coefficient of Variation. Plasma concentrations are expressed in nanograms per ml, MQL stands for Minimum Quantifiable Level and ND stands for None Detected.

TABLE 1

(Comparative formulation 1)

| Times (h) Volunteer | 0.0 | 0.25 | 0.50 | 0.75 | 1.0 | 1.50 | 2.0 | 3.0 | 4.0 | 6.0 | 8.0 | 10.0 |
| --- | --- | --- | --- | --- | --- | --- | --- | --- | --- | --- | --- | --- |
| 1. DC | ND | ND | ND | ND | ND | 5.71 | 17.1 | 60.3 | 59.9 | 30.4 | 16.9 | 8.63 |
| 2. TE | <MQL | <MQL | 3.29 | 23.7 | 29.0 | 34.9 | 37.8 | 34.3 | 29.9 | 17.4 | 12.9 | 12.2 |
| 3. VG | ND | ND | 7.22 | 18.7 | 25.2 | 22.9 | 23.9 | 28.2 | 30.2 | 19.9 | 8.64 | 7.53 |
| 4. NC | ND | ND | ND | ND | ND | 16.1 | 14.7 | 23.7 | 24.4 | 27.7 | 14.4 | 9.90 |
| 5. NH | ND | ND | ND | ND | 4.64 | 7.15 | 21.4 | 27.7 | 32.1 | 14.6 | 10.5 | 6.26 |
| 6. SO | ND | ND | <MQL | 4.38 | 4.28 | 5.69 | 7.24 | 7.92 | 5.61 | <MQL | <MQL | 3.88 |
| 7. AQ | ND | ND | 6.34 | 13.9 | 16.8 | 16.3 | 16.1 | 12.9 | 9.66 | 4.64 | 2.10 | ND |
| 8. SW | ND | ND | ND | ND | 7.98 | 28.6 | 24.0 | 27.0 | 29.7 | 15.4 | 8.09 | 6.10 |
| Mean | — | — | 2.28 | 7.58 | 10.98 | 17.16 | 20.28 | 27.75 | 27.68 | 16.43 | 9.36 | 6.81 |
| S.D. | — | — | 3.01 | 9.73 | 11.31 | 10.97 | 8.97 | 15.73 | 16.45 | 10.03 | 5.53 | 3.74 |
| C of V | — | — | 132 | 128 | 102 | 63 | 44 | 56 | 59 | 61 | 59 | 54 |

TABLE 2

(Formulation of Example 1)

| Times (h) Volunteer | 0.0 | 0.25 | 0.50 | 0.75 | 1.0 | 1.50 | 2.0 | 3.0 | 4.0 | 6.0 | 8.0 | 10.0 |
| --- | --- | --- | --- | --- | --- | --- | --- | --- | --- | --- | --- | --- |
| 1. DC | ND | ND | 14.3 | 34.1 | 52.5 | 76.5 | 96.6 | 98.1 | 79.2 | 40.8 | 25.2 | 15.4 |
| 2. TE | <MQL | <MQL | <MQL | 6.40 | 19.4 | 64.3 | 63.4 | 56.7 | 49.8 | 26.5 | 12.4 | 9.10 |
| 3. VG | ND | ND | 43.0 | 41.4 | 69.2 | 88.3 | 83.9 | 76.6 | 46.5 | 27.1 | 11.4 | 6.35 |
| 4. NC | ND | ND | ND | 24.8 | 45.5 | 43.4 | 25.8 | 62.5 | 54.3 | 27.2 | NS | NS |
| 5. NH | ND | ND | 10.9 | 28.1 | 47.5 | 48.1 | 37.9 | 27.6 | 25.2 | 14.0 | 7.23 | 5.29 |
| 6. SO | ND | ND | 3.49 | 56.0 | 70.3 | 46.3 | 38.9 | 30.2 | 24.2 | 15.1 | 10.1 | 7.23 |

TABLE 2-continued (Formulation of Example 1)

| Times (h) Volunteer | 0.0 | 0.25 | 0.50 | 0.75 | 1.0 | 1.50 | 2.0 | 3.0 | 4.0 | 6.0 | 8.0 | 10.0 |
|---|---|---|---|---|---|---|---|---|---|---|---|---|
| 7. AQ | ND | ND | ND | 6.97 | 9.72 | 31.3 | 32.5 | 67.6 | 57.6 | 20.5 | 11.4 | 7.06 |
| 8. SW | ND | ND | ND | 19.9 | 63.5 | 79.3 | 63.0 | 49.4 | 35.1 | 17.0 | 10.7 | 6.76 |
| Mean | — | — | 9.13 | 27.20 | 47.20 | 59.68 | 55.25 | 58.58 | 46.48 | 23.52 | 12.63 | 8.17 |
| S.D. | — | — | 14.72 | 16.82 | 22.33 | 20.32 | 25.66 | 23.41 | 18.30 | 8.83 | 5.77 | 3.38 |
| C of V | — | — | 161 | 61 | 47 | 34 | 46 | 39 | 39 | 37 | 45 | 41 |

The plasma concentrations of Compound A from both of the formulations in the foregoing study were processed using the bioavailability program "BIOMU" which determines the maximum plasma concentration ($C_{max}$) and the time to reach maximum concentration ($t_{max}$). The area under the plasma concentration vs. time curve from zero time to the last sampling point (AUC) gives a measure of the total medicament plasma concentration, or total bioavailability of the medicament, over the entire sampling period and is calculated using the trapezoidal rule. The results so-obtained are given in Table 3.

TABLE 3

| | Comparative Formulation 1 | | | Formulation of Example 1 | | |
|---|---|---|---|---|---|---|
| Vol. | $C_{max}$ | $t_{max}$ | AUC | $C_{max}$ | $t_{max}$ | AUC |
| 1. DC | 60.30 | 3.00 | 269.06 | 98.10 | 3.00 | 506.79 |
| 2. TE | 37.80 | 2.00 | 216.12 | 64.30 | 1.50 | 308.13 |
| 3. VG | 30.20 | 4.00 | 183.42 | 88.30 | 1.50 | 383.83 |
| 4. NC | 27.70 | 6.00 | 173.48 | 62.50 | 3.00 | 262.66 |
| 5. NH | 32.10 | 4.00 | 153.68 | 48.10 | 1.50 | 193.19 |
| 6. SO | 7.92 | 3.00 | 39.69 | 70.30 | 1.00 | 217.69 |
| 7. AQ | 16.80 | 1.00 | 72.46 | 67.60 | 3.00 | 270.27 |
| 8. SW | 29.70 | 4.00 | 159.92 | 79.30 | 1.50 | 279.90 |
| Mean | 30.32 | 3.38 | 158.48 | 72.31 | 2.00 | 302.81 |
| S.D. | 15.35 | 1.51 | 73.61 | 15.78 | 0.85 | 100.47 |
| C of V | 51 | 45 | 46 | 22 | 42 | 33 |

These data show that Formulation B, the formulation within the ambit of the invention, has a faster release rate and produces a higher peak plasma concentration than Formulation A (Comparative Formulation 1). The bioavailability, expressed in terms of the AUC values, of Formulation B relative to Comparative Formulation 1 (Formulation A) was 191%.

It is apparent from the results of the above-described studies that the new nonpareil formulations give improved release of medicament and greater bioavailability than conventional encapsulated dry powder capsules.

Following the same procedure described above, a further comparative study between the release rates of Compound A from Comparative Formulation 1 and from a batch of the formulation of Example 5 was carried out using 32 male volunteers.

Analysis of the plasma concentration data so-obtained as before afforded the $C_{max}$, $t_{max}$ and AUC data for each formulation summarized in Table 4.

TABLE 4

| | Comp. Form. 1 | | | Batch Ex. 5 | | |
|---|---|---|---|---|---|---|
| | $C_{max}$ | $t_{max}$ | AUC | $C_{max}$ | $t_{max}$ | AUC |
| Mean | 42.06 | 2.93 | 201.7 | 65.35 | 2.35 | 269.0 |
| S.D. | 27.36 | 1.61 | 128.2 | 30.84 | 1.44 | 111.0 |
| C of V | 65 | 55 | 64 | 47 | 61 | 41 |

For purposes of comparison of in vitro release rates of Compounds D and E from the formulations of Examples 8 and 9, respectively, Comparative Formulations 2 and 3, comprising conventional capsule compositions were formulated as follows and fed into size 1 gelatine capsules. All weights are in milligrams per dose.

| | Comparative Formulation | |
|---|---|---|
| Ingredient | 2 | 3 |
| Compound D | 100 | — |
| Compound E | — | 120 |
| Starch BP | 74 | 110 |
| Lactose BP | 100 | 113 |
| Starch BP | 14 | 3.5 |
| Magnesium Stearate | 2 | 3.5 |
| Total | 290 | 350 |

Figure 2:
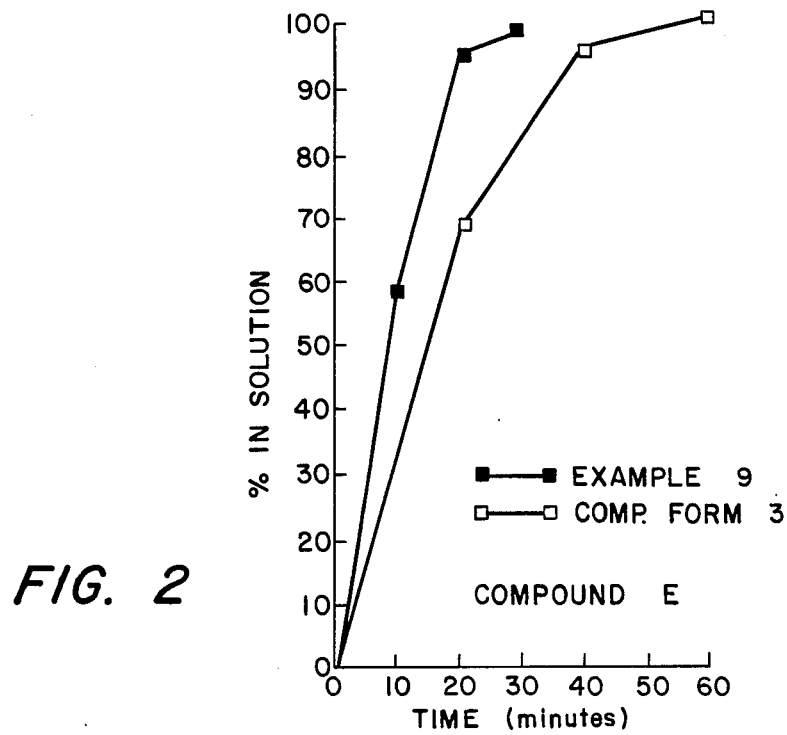

Test capsules weighted with a wire wrapped around the capsules to serve to anchor the capsules, were placed in a round bottom vessel containing 900 ml. of phosphate buffer at pH 8.9 for formulations containing compound D, and pH 8 for formulations containing compound E immersed in a constant temperature bath at 37° C. and fitted with a paddle stirrer and stirring motor. 10 ml. aliquots were withdrawn periodically from the stirred solution, and the amount of active ingredient in each aliquot was determined by u.v. spectrophotometric analysis. The results obtained comparing the release rates of the formulation of Example 8 and Comparative Formulation 2 are shown in FIG. 1, and the results obtained comparing the release rates of the formulation of Example 9 with Comparative Formulation 3 are given in FIG. 2. These results show that compounds D and E are released more rapidly from formulations within the ambit of this invention (Examples 8 and 9) than from standard powder formulations (comparative formulations 2 and 3).

We claim:

1. A pharmaceutical composition for oral administration comprising a plurality of nonpareil beads having, as a single coating bound thereto, by a binder soluble in water and aqueous media at all pH values normally found in the gastrointestinal tract, a medicament selected from the group consisting of 17α-pregna-2,4-diene-20-yno[2,3-d]isoxazol-17-ol, 17β-hydroxy-17α-methylandrostano[3,2-c]pyrazole, 17β-hydroxy-17α-ethynyl-4-androsteno[3,2-c]-2'-(para-fluorophenyl)-pyrazole, 4α,5α-epoxy-17β-hydroxy-4,17-dimethyl-3-oxoandrostane-2α-carbonitrile and 4α,5α-epoxy-17β-hydroxy-3-oxoandrostane-2α-carbonitrile.

2. A pharmaceutical composition according to claim 1 wherein a unit dosage amount of said plurality of beads is enclosed within a gastric juice soluble material.

3. A pharmaceutical composition according to claim 2 wherein said gastric juice-soluble material is in the form of a gelatine capsule.

4. A pharmaceutical composition according to claim 2 wherein the beads further include a pharmacologically acceptable wetting agent.

5. A pharmaceutical preparation according to claim 4 wherein the binder comprises hydroxypropylmethylcellulose, polyvinylpyrrolidone or a mixture thereof.

6. A pharmaceutical preparation according to claim 4 wherein the binder is a water-soluble polysaccharide or a sugar derived from a sugar syrup.

7. A pharmaceutical composition according to claim 5 wherein the medicament is 17α-pregna-2,4-diene-20-yno[2,3-d]isoxazol-17-ol.

* * * * *